United States Patent
Wang et al.

(10) Patent No.: US 9,938,213 B2
(45) Date of Patent: Apr. 10, 2018

(54) METHODS FOR REMOVING ACIDIC IMPURITIES FROM HALOGENATED PROPENES

(71) Applicant: Honeywell International, Inc., Morris Plains, NJ (US)

(72) Inventors: Haiyou Wang, Amherst, NY (US); Hsueh Sung Tung, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/232,089

(22) Filed: Aug. 9, 2016

(65) Prior Publication Data

US 2017/0050905 A1 Feb. 23, 2017

Related U.S. Application Data

(60) Provisional application No. 62/206,916, filed on Aug. 19, 2015.

(51) Int. Cl.
*C07C 17/389* (2006.01)
*C07C 21/18* (2006.01)

(52) U.S. Cl.
CPC .................. *C07C 17/389* (2013.01)

(58) Field of Classification Search
CPC ....... C07C 17/389; C07C 21/18; C07C 17/42; B01D 53/263; B01D 53/28; B01D 2251/302; B01D 2251/402; B01D 2251/60; B01D 2252/10; B01D 2252/103; B01D 2256/26; B01D 2257/80
See application file for complete search history.

(56) References Cited

U.S. PATENT DOCUMENTS

| | | | |
|---|---|---|---|
| 8,653,311 | B2 | 2/2014 | Hulse et al. |
| 2009/0266745 | A1 | 10/2009 | Kanazirev et al. |
| 2012/0256120 | A1* | 10/2012 | Bouvier ............. C09K 5/045 252/68 |
| 2013/0158305 | A1* | 6/2013 | Takahashi .......... B01D 53/263 570/177 |
| 2015/0197468 | A1 | 7/2015 | Cottrell et al. |

FOREIGN PATENT DOCUMENTS

| | | |
|---|---|---|
| CN | 103896214 A | 7/2014 |
| CN | 104529692 A | 4/2015 |
| EP | 2339271 A1 | 6/2011 |
| WO | 2013128225 A1 | 9/2013 |
| WO | 2014158663 A1 | 10/2014 |

* cited by examiner

*Primary Examiner* — Jafar Parsa
(74) *Attorney, Agent, or Firm* — Bruce O. Bradford

(57) ABSTRACT

This invention pertains to a method for removing acidic impurity from halogenated olefins, especially methods for removing acidic impurity from halogenated propenes, and even more particularly to methods for removing acidic impurity from 1,3,3,3-tetrafluoro-1-propene (HFO-1234ze), 2,3,3,3-tetrafluoro-1-propene (HFO-1234yf), 1-chloro-3,3,3-trifluoro-1-propene (HCFO-1233zd), and 2-chloro-3,3,3-trifluoro-1-propene (HCFO-1233xf). The method is conducted by passing the halogenated olefin stream, in liquid or gas form, through a solid adsorbent bed, which contains at least one acid reactive agent.

19 Claims, No Drawings

METHODS FOR REMOVING ACIDIC IMPURITIES FROM HALOGENATED PROPENES

CROSS-REFERENCE TO RELATED APPLICATIONS

This application claims domestic priority from commonly owned, U.S. Provisional Patent Application Ser. No. 62/206,916, filed 19 Aug. 2015, the disclosure of which is hereby incorporated herein by reference.

FIELD OF THE INVENTION

The invention pertains to a method for removing acidic impurities from halogenated olefins, especially methods for removing acidic impurities from halogenated propenes, and even more particularly to methods for removing acidic impurities from 1,3,3,3-tetrafluoro-1-propene (HFO-1234ze), 2,3,3,3-tetrafluoro-1-propene (HFO-1234yf), 1-chloro-3,3,3-trifluoro-1-propene (HCFO-1233zd), and 2-chloro-3,3,3-trifluoro-1-propene (HCFO-1233xf).

BACKGROUND OF THE INVENTION

Chlorofluorocarbons (CFCs) like trichlorofluoromethane and dichlorodifluoro-methane have been used as refrigerants, blowing agents and diluents for gaseous sterilization. In recent years, there has been widespread concern that certain chlorofluorocarbons might be detrimental to the Earth's ozone layer. As a result, there is a worldwide effort to use halocarbons which contain fewer or no chlorine substituents.

Accordingly, the production of hydrofluorocarbons, or compounds containing only carbon, hydrogen and fluorine, has been the subject of increasing interest to provide environmentally desirable products for use as solvents, blowing agents, refrigerants, cleaning agents, aerosol propellants, heat transfer media, dielectrics, fire extinguishing compositions and power cycle working fluids. In this regard, trans-1,3,3,3-tetrafluoropropene (trans-1234ze or 1234zeE), trans-1-chloro-3,3,3-trifluoropropene (trans-1233zd or 1233zdE), and 2,3,3,3-tetrafluoropropene (1234yf) are among a number of products that have been or are being commercialized for various applications.

There are numerous processes directed to the manufacture of fluorinated organic compounds and to compositions containing such compounds. Many of these processes involve the reaction of an organic compound, such as a chloroalkane or chloroalkene, with hydrogen fluoride (HF) in the presence of a fluorination catalyst. In many of these processes, water is present in one or more of the reaction product streams containing the desired fluorinated organic compound. This water may originate as an impurity in the reactants or other starting materials. The water also may be formed as a byproduct from the reaction process, including reaction of HF with the catalyst, and/or as a product of the catalyst regeneration process. Moreover, the water may be entrained from an upstream unit operation such as a caustic solution scrubber in which acidic gases are neutralized and removed.

To remove the water included in acid-free hydrofluorocarbon and/or hydrochloro-fluorocarbon streams, concentrated sulfuric acid is often used as a drying agent since it has a very strong affinity for water. The absorption of water into sulfuric acid can be realized in a typical drying acid system, which typically consists of a drying tower, acid pump tank, acid pump, acid cooler, piping, and instrumentation and controls. A typical drying tower is a vertical cylindrical vessel designed to contact process gas and strong sulfuric acid (93% to 98.5% $H_2SO_4$) for the purpose of drying the gas.

Recently, Applicants have unexpectedly discovered that certain halogenated propenes are reactive with sulfuric acid, generating small amounts of acids, non-exclusively including HF and HCl, which could cause corrosion to the downstream processing equipment such as distillation columns, pumps, storage tanks, etc. Non-limiting examples of these halogenated propenes include 1,3,3,3-tetrafluoropropene (1234ze), 1-chloro-3,3,3-trifluoropropene (1233zd), and 2-chloro-3,3,3-trifluoropropene (1233xf). The first two can be used as final products, while the third is a useful intermediate for making 2,3,3,3-tetrafluoropropene. Therefore, there is a need for means by which the acid(s) present in various halogenated propene streams can be removed using a cost-effective method.

SUMMARY OF THE INVENTION

The present inventors have come to appreciate a need in the art for a method of removing acidic impurities included in halogenated propenes, non-exclusively including 1,3,3,3-tetrafluoropropene (1234ze), 2,3,3,3-tetrafluoro-1-propene (1234yf), 1-chloro-3,3,3-trifluoropropene (1233zd), and 2-chloro-3,3,3-trifluoropropene (1233xf). Non-limiting examples of acidic impurities include hydrogen fluoride (HF), hydrogen chloride (HCl), sulfuric acid ($H_2SO_4$), trifluoroacetic acid ($CF_3COOH$), and mixtures of two or more of such acids.

It has been found that this need can be satisfied by passing the halogenated propene stream in liquid or gas form through a solid adsorbent bed, which contains at least one acid reactive agent. The acid reactive agent can be selected from the group consisting of metal oxides such as aluminum oxide, alkaline earth metal oxide, alkali metal oxide, metal hydroxides such as aluminum hydroxide, alkaline earth metal hydroxide, and alkali metal hydroxide, aluminosilicate minerals such as andalusite, kyanite, sillimanite, calcium aluminosilicate, sodium aluminosilicate, silicon oxide, and their various combinations.

In view that water may be generated from the reaction between acid and acid reactive agent, preferably, the solid adsorbent bed additionally contains a water absorbing agent. The water absorbing agent can be selected from the group comprising inorganic salts such as magnesium sulfate, calcium sulfate (Drierite), and calcium chloride, molecular sieves (molsiv) such as 3A, 4A, 5A, AW500, XH-7, XH-9, and 13X, silica gel, activated carbons, and various combinations of thereof. Preferably, the solid adsorbent bed contains an acid reactive agent at the top section and a water absorbing agent at the bottom section, and the halogenated propene stream enters the solid adsorbent bed from the top section. In preferred embodiment, activated alumina is used as acid reactive agent, 3A or XH-9 as water absorbing agent. By applying this teaching, a halogenated propene stream that is essentially free of acid can be achieved.

Thus, one embodiment of the invention is a method for removing acidic impurity from halogenated olefins comprising contacting a liquid or gas stream comprising a halogenated olefin by passing the stream through a solid adsorbent bed which contains at least one acid reactive agent and wherein the solid adsorbent bed additionally contains a water absorbing agent; and wherein the acidic impurities are selected from the group consisting of hydrogen fluoride (HF), hydrogen chloride (HCl), sulfuric acid ($H_2SO_4$), trifluoroacetic acid ($CF_3COOH$), and mixtures of two or more of these acids.

One embodiment of the invention is a method for removing acidic impurity from halogenated olefins comprising contacting a liquid or gas stream comprising a halogenated olefin by passing the stream through a solid adsorbent bed comprising at least one acid reactive agent and at least one water absorbing agent;

wherein the acidic impurities are selected from the group consisting of hydrogen fluoride (HF), hydrogen chloride (HCl), sulfuric acid ($H_2SO_4$), trifluoroacetic acid ($CF_3COOH$), and mixtures of two or more of these acids; and wherein the halogenated olefins comprise halogenated propenes selected from the group consisting of 1,3,3,3-tetrafluoro-1-propene (HFO-1234ze), 2,3,3,3-tetrafluoro-1-propene (HFO-1234yf), 1-chloro-3,3,3-trifluoro-1-propene (HCFO-1233zd), and 2-chloro-3,3,3-trifluoro-1-propene (HCFO-1233xf).

In certain embodiments, the acid reactive agent is selected from:

(a) the group consisting of metal oxides, alkaline earth metal oxides, alkali metal oxides, and mixtures thereof;

(b) the group consisting of metal hydroxides, alkaline earth metal hydroxides, alkali metal hydroxides, and mixtures thereof;

(c) an aluminosilicate mineral selected from the group consisting of andalusite, kyanite, sillimanite, calcium aluminosilicate, sodium aluminosilicate, and mixtures thereof;

(d) silicon oxide; and (e) activated alumina.

In certain embodiments, the water absorbing agent is selected from:

(a) the group consisting of inorganic salts, magnesium sulfate, calcium sulfate, calcium chloride, and combinations thereof;

(b) the group consisting of molecular sieves 3A, 4A, 5A, AW500, XH-7, XH-9, 13X and combinations thereof; and (c) the group consisting of silica gel, activated carbon, and combinations of thereof.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

The present invention can be generally described as a method for removing acidic impurities, non-exclusively including hydrogen fluoride (HF), hydrogen chloride (HCl), sulfuric acid ($H_2SO_4$), and trifluoroacetic acid ($CF_3COOH$) present in a liquid or gas stream of halogenated propene, non-exclusively selected from the group comprising 1,3,3,3-tetrafluoropropene (1234ze), 2,3,3,3-tetrafluoro-1-propene (1234yf), 1-chloro-3,3,3-trifluoropropene (1233zd), and 2-chloro-3,3,3-trifluoropropene (1233xf), by passing the halogenated propene stream in liquid or gas form through a solid adsorbent bed containing at least an acid reactive agent.

In some embodiments of this invention, the organic portion of halogenated propene stream is a purified product comprising a single halogenated propene (e.g., trans-1234ze, trans-1233zd, 1233xf, or 1234yf). In some embodiments of this invention, the organic portion of halogenated propene stream is a crude product comprising one or more halogenated propenes, and one or more halogenated propanes (e.g., a mixture of trans-1234ze, cis-1234ze, 245fa, etc.). In some embodiments of this invention, the passage of halogenated propene stream through the solid adsorbent bed is a once-through process, in which the organic stream is passed through the adsorbent bed only for a single time. In some embodiments of this invention, the passage of halogenated propene stream through the solid adsorbent bed is a circulation process, in which the organic stream is circulated through the adsorbent bed for multiple times.

The acid reactive agent can be selected from the group comprising metal oxides such as aluminum oxide (alumina), alkaline earth metal oxide, alkali metal oxide, metal hydroxides such as aluminum hydroxide, alkaline earth metal hydroxide, and alkali metal hydroxide, aluminosilicate minerals such as andalusite, kyanite, sillimanite, calcium aluminosilicate, sodium aluminosilicate, silicon oxide, and their various combinations. In some preferred embodiments, alumina is used as acid reactive agent. In some even more preferred embodiments, activated alumina is used. Activated alumina is a porous, granular substance, and can be manufactured from aluminum hydroxide by dehydroxylating it in a way that produces a highly porous material. Activated alumina can have a surface area significantly over 200 $m^2/g$.

In view that water may be generated from the reaction between acid and acid reactive agent, preferably, the solid adsorbent bed additionally contains a water absorbing agent. The water absorbing agent can be selected from the group comprising inorganic salts such as magnesium sulfate, calcium sulfate (Drierite), and calcium chloride, molecular sieves such as 3A, 4A, 5A, AW500, XH-7, XH-9, and 13X, silica gel, activated carbons, and various combinations of thereof.

In some preferred embodiments, a molecular sieve is used as water absorbing agent. A molecular sieve is a material with very small holes of precise and uniform size. These holes are small enough to block large molecules, while allowing small molecules to pass. In an even more preferred embodiment, 3A is used for once-through process. In another more preferred embodiment, XH-9 is used for circulation process.

When both acid reactive agent and water absorbing agent are present in the solid adsorbent bed, preferably, the acid reactive agent is at the top section and the water absorbing agent at the bottom section, and the halogenated propene stream enters the solid adsorbent bed from the top section (in other words, the acid reactive agent contacts the organic stream first). The amount of water absorbing agent layer relative to acid reactive agent layer can be determined experimentally or based on their adsorption capacities. In some embodiments of this invention, the volume of water absorbing agent layer is 10 to 60%. In some embodiments of this invention, the volume of water absorbing agent layer is 30 to 50%.

The contact between the halogenated propene stream and the acid reactive agent (or both the acid reactive agent and the water absorbing agent) may be conducted in any suitable vessel or reactor, which should preferably be constructed from materials that are resistant to the corrosive effects of various acids including stainless steel, Hastelloy, Inconel, Incoloy, Monel, or fluoropolymer-lined.

In some embodiments of this invention, the temperature during the contacting step is from about −20° C. to about 200° C. In some embodiments of this invention, the temperature during the contacting step is from about 0° C. to about 100° C. In some embodiments of this invention, the temperature during the contacting step is from about 10° C. to about 50° C. In some embodiments of this invention, the temperature during the contacting step is about room temperature. The pressure during the contacting step is not critical and can be in the range of from about 10 kPa to about 3000 kPa.

During the contacting step, the mixture of halogenated propene and acidic impurity is scrubbed with acid reactive agent in the contacting vessel, and the acidic impurity is removed. In some embodiments of this invention, the concentration of at least one acidic impurity in the mixture is reduced to 0.5 ppm or less. In some embodiments of this invention, the concentration of at least one acidic impurity in the mixture is reduced to 0.1 ppm or less. In some embodiments of this invention, the concentration of at least one acidic impurity in the mixture is reduced to 0.05 ppm or less. In some embodiments of this invention, the amount of at least one acidic impurity in the mixture is reduced by at least about 50% by weight relative to the amount originally present. In some embodiments of this invention, the amount of at least one acidic impurity in the mixture is reduced by at least about 80% by weight relative to the amount originally present. In some embodiments of this invention, the amount of at least one acidic impurity in the mixture is reduced by at least about 95% by weight relative to the amount originally present.

The halogenated propene having reduced concentration of the acidic impurity obtained from the contacting step can be recovered using techniques well-known in the art, such as condensation or distillation. In some embodiments of this invention, the halogenated propene obtained from the contacting step may be further purified by fractional distillation.

EXAMPLES

The following non-limiting examples serve to illustrate the invention.

Example 1—The Removal of Acid(s) Included in Crude 1234zeE Over Various Solid Adsorbents 15 ml 95% $H_2SO_4$ was charged into a PFA reactor vessel, which was heated to 38° C. using an oil bath. The temperature was maintained at the set point for 30 min before the addition of organic was started to ensure the $H_2SO_4$ was uniformly heated to the set point. Magnetic stirring was applied to the reactor vessel throughout the experiment to ensure constant temperature and mixing of the organic and the $H_2SO_4$. The reactor outlet was connected to a solid adsorbent column and then a PFA trap containing 20 ml DI-water to absorb acids (if any). At the end of experiments, the contents of the PFA-$H_2SO_4$ reactor vessel were analyzed by $^{19}F$-NMR and the contents of the DI-Water trap by IC.

In this example, the organic was crude 1234zeE, which contained 45-60% 1234zeE, 30-45% 245fa, and 5-15% 1234zeZ. The solid adsorbents tested include silica gel, alumina, XH-9, 3A and 4A molsiv. As shown in Table 1, HF was indeed formed in sulfuric acid reactor. Nevertheless, its level in DI water trap (i.e., in the outlet of solid adsorbent column) was significantly lower. The concentration of HF in organic stream after solid adsorbent column was calculated and listed in the last column of Table 1. One can see negligible amount of HF was detected when alumina, 3A molsiv, or 4A molsiv was used.

TABLE 1

| Org. type | Org. fed, g | $H_2SO_4$ acid conc., wt % | $H_2SO_4$ acid wt, g | Temp., ° C. | Adsorbent | Composition in sulfuric acid reactor vessel, ppm | | | Composition in DI water trap, ppm | | HF in exiting organic, ppm |
|---|---|---|---|---|---|---|---|---|---|---|---|
| | | | | | | Organic | $FHSO_3$ | HF | $F^-$ | $Si^{4+}$ | |
| Crude 1234zeE | 90.0 | 95 | 25.0 | 38 | $SiO_2$ (20 ml) | 2936.0 | 376.9 | 14.1 | 0.53 | 0.57 | 0.12[1] |
| | 439.4 | 95 | 25.8 | 38 | XH-9 (40 ml) | 4073.5 | 505.7 | 21.5 | 6.45 | — | 0.30 |
| | 409.5 | 95 | 27.9 | 38 | Alumina (40 ml) | 6420.9 | 2691.6 | 26.0 | 0.19 | — | 0.01 |
| | 382.9 | 95 | 26.1 | 38 | 3A (40 ml) | 9697.6 | 1375.5 | 22.7 | 0.34 | — | 0.02 |
| | 337.2 | 95 | 24.5 | 38 | 4A (40 ml) | 4033.3 | 1454.7 | 15.6 | 0.20 | — | 0.01 |

[1] The acidity was most likely originated from $SiF_4$ hydrolysis as evidence by the presence of silicon ion in DI water Example 2—The Removal of Acid(s) Included in Crude 1234zeE Over Alumina 15 ml 95% $H_2SO_4$ was charged into a PFA reactor vessel, which was heated to 38° C. using an oil bath. The temperature was maintained at the set point for 30 min before the flow of organic was started at an average flow rate of 106 g/h to ensure the $H_2SO_4$ was uniformly heated to the set point. Magnetic stirring was applied to the reactor vessel throughout the experiment to ensure constant temperature and mixing of the organic and the $H_2SO_4$. The outlet from the reactor vessel was connected to an activated alumina column containing 20 ml (15.1 g) alumina and then to a PFA trap containing 40 ml DI-water to "scrub" the reactor effluent gases. During experiments, reactor effluent samples (i.e., alumina column inlet samples) and DI water samples (i.e., alumina column outlet samples) were periodically taken and analyzed by means of IC to determine the HF levels in the inlet and outlet of alumina column.

In this example, the organic was crude 1234zeE, which contained 45-60% 1234zeE, 30-45% 245fa, and 5-15%

1234zeZ. As shown in Table 2, while the HF concentration in the inlet of alumina column was about 22 ppm on average, negligible amount of HF was detected in the outlet of the column, once again indicating alumina was efficient for removing HF. Calculation using total organic amount passed through the alumina column and averaged HF concentrations in the inlet and the outlet of the alumina column showed the amount of HF adsorbed reached 9.2% of alumina weight after 25 days on stream.

TABLE 2

| Day no. | Org. amt. passed, g | HF concentration, ppm | |
|---|---|---|---|
| | | Column inlet | Column outlet |
| 1 | 1610 | 19.7 | 0.013 |
| 2 | 2195 | 20.3 | 0.005 |
| 3 | 2380 | 30.2 | 0.002 |
| 4 | 2440 | 27.2 | 0.002 |
| 5 | 2110 | 28.7 | 0.004 |
| 6 | 2610 | 31.3 | 0.001 |
| 7 | 2715 | 34.1 | 0.001 |
| 8 | 2545 | 24.4 | 0.001 |
| 9 | 2385 | 46.0 | 0.002 |
| 10 | 2415 | 26.2 | 0.001 |
| 11 | 2590 | 28.1 | 0.001 |
| 12 | 2835 | 31.7 | 0.001 |
| 13 | 2425 | 32.0 | 0.002 |
| 14 | 3010 | 55.3 | 0.001 |
| 15 | 3125 | 7.8 | 0.000 |
| 16 | 2855 | 2.8 | 0.000 |
| 17 | 2370 | 1.9 | 0.001 |
| 18 | 2815 | 8.8 | 0.001 |
| 19 | 2700 | 7.7 | 0.006 |
| 20 | 2115 | 9.9 | 0.003 |
| 21 | 2720 | 2.6 | 0.001 |
| 22 | 2035 | 22.4 | 0.001 |
| 23 | 2470 | 9.2 | 0.004 |
| 24 | 2590 | 8.8 | 0.001 |
| 25 | 2150 | 43.5 | 0.081 |
| Average | 2488 | 22.4 | 0.005 |

Example 3—The Removal of Acid(s) Included in 1234zeE Product 15 ml 95% $H_2SO_4$ was charged into a PFA reactor vessel, which was heated to 38° C. using an oil bath. The temperature was maintained at the set point for 30 min before the flow of organic was started at an average flow rate of 35 g/h to ensure the $H_2SO_4$ was uniformly heated to the set point. Magnetic stirring was applied to the reactor vessel throughout the experiment to ensure constant temperature and mixing of the organic and the $H_2SO_4$. The outlet from the reactor vessel was connected to a combined 20 ml alumina/20 ml XH-9 molsiv column and then a PFA trap containing 20 ml DI-water to absorb acids (if any). At the end of experiments, which lasted for 59 hours, the contents of the DI-Water trap were analyzed by IC.

In this example, the organic was 1234zeE product, which was 99.9+% pure. The IC analysis results showed negligible HF (<0.1 ppm) was present in DI water.

Example 4—The Removal of Acid(s) Included in 1233xf Intermediate 15 ml 95-98% $H_2SO_4$ was charged into a PFA reactor vessel, which was heated to 38° C. using an oil bath. The temperature was maintained at the set point for 30 min before the flow of organic was started at an average flow rate of 30 g/h to ensure the $H_2SO_4$ was uniformly heated to the set point. Magnetic stirring was applied to the reactor vessel throughout the experiment to ensure constant temperature and mixing of the organic and the $H_2SO_4$. The outlet from the reactor vessel was connected to a combined 20 ml alumina/20 ml 3A molsiv column and then a PFA trap containing 20 ml DI-water to absorb acids (if any). During experiments, reactor effluent samples (i.e., alumina column inlet samples) and DI water samples (i.e., alumina column outlet samples) were periodically taken and analyzed by means of IC to determine the HF levels in the inlet and outlet of alumina column.

In this example, the organic was 1233xf intermediate, which was 99+% pure. The IC analysis results showed the average concentrations of HF and HCl in the inlet of alumina/3A column were about 1, and 65 ppm, respectively, but negligible amounts (<0.1 ppm) of HF and HCl were detected in the outlet of the column.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A method for removing acidic impurity from halogenated olefins comprising contacting a liquid or gas stream comprising a halogenated olefin by passing the stream through a solid adsorbent bed which contains at least one acid reactive agent and wherein the solid adsorbent bed additionally contains a water absorbing agent; and wherein the acidic impurities are selected from the group consisting of hydrogen fluoride (HF), hydrogen chloride (HCl), sulfuric acid ($H_2SO_4$), trifluoroacetic acid ($CF_3COOH$), and mixtures of two or more of these acids; and
   wherein the solid adsorbent bed has the acid reactive agent at the top section and the water absorbing agent at the bottom section, and the halogenated olefin stream enters the solid adsorbent bed at the top section.

2. The method of claim 1, wherein the halogenated olefins comprise halogenated propenes.

3. The method of claim 2, wherein the halogenated propenes are selected from the group consisting of 1,3,3,3-tetrafluoro-1-propene (HFO-1234ze), 2,3,3,3-tetrafluoro-1-propene (HFO-1234yf), 1-chloro-3,3,3-trifluoro-1-propene (HCFO-1233zd), and 2-chloro-3,3,3-trifluoro-1-propene (HCFO-1233xf).

4. The method of claim 1, wherein the acid reactive agent is selected from the group consisting of metal oxides, alkaline earth metal oxides, alkali metal oxides, and mixtures thereof.

5. The method of claim 1, wherein the acid reactive agent is selected from the group consisting of metal hydroxides, alkaline earth metal hydroxides, alkali metal hydroxides, and mixtures thereof.

6. The method of claim 1, wherein the acid reactive agent comprises an aluminosilicate mineral selected from the group consisting of andalusite, kyanite, sillimanite, calcium aluminosilicate, sodium aluminosilicate, and mixtures thereof.

7. The method of claim 1, wherein the acid reactive agent comprises silicon oxide.

8. The method of claim 1, wherein the acid reactive agent comprises activated alumina.

9. The method of claim 1, wherein the volume of the water absorbing agent layer is from 10% to 60%.

10. The method of claim 1, wherein the volume of the water absorbing agent layer is from 30% to 50%.

11. The method of claim 1, wherein the water absorbing agent is selected from the group consisting of inorganic salts, magnesium sulfate, calcium sulfate, calcium chloride, and mixtures thereof.

12. The method of claim 1, wherein the water absorbing agent is selected from the group consisting of molecular sieves 3A, 4A, 5A, AW500, XH-7, XH-9, 13X and mixtures thereof.

13. The method of claim 1, wherein the water absorbing agent is selected from the group consisting of silica gel, activated carbons, and mixtures thereof.

14. The method of claim 1, wherein activated alumina is used as the acid reactive agent and molecular sieves 3A or XH-9 are used as the water absorbing agent.

15. The method of claim 1, wherein during the contacting step, the mixture of halogenated propene and acidic impurity is scrubbed with acid reactive agent in the contacting vessel.

16. The method of claim 15, wherein the concentration of at least one acidic impurity in the mixture is reduced to 0.5 ppm or less.

17. The method of claim 15, wherein the amount of at least one acidic impurity in the mixture is reduced by at least about 50% by weight relative to the amount originally present.

18. The method of claim 1, wherein the passage of halogenated propene stream through the solid adsorbent bed is a once-through process, in which the organic stream is passed through the adsorbent bed only for a single time.

19. The method of claim 1, wherein the passage of halogenated propene stream through the solid adsorbent bed is a circulation process, in which the organic stream is circulated through the adsorbent bed for multiple times.

* * * * *